United States Patent [19]

Yamamoto et al.

[11] 4,451,271

[45] May 29, 1984

[54] METHOD OF SEPARATING LIQUID DROPS FROM OFF GAS

[75] Inventors: Satoshi Yamamoto; Osamu Hase; Tamostu Kawata, all of Ibaragi, Japan

[73] Assignee: Yukamelamin Company, Limited, Ibaragi, Japan

[21] Appl. No.: 364,272

[22] Filed: Apr. 1, 1982

[30] Foreign Application Priority Data

Apr. 2, 1981 [JP] Japan .................................. 56-49693

[51] Int. Cl.³ .............................................. B01D 47/00
[52] U.S. Cl. .............................................. 55/84; 55/96; 55/243; 544/203
[58] Field of Search ................. 55/68, 82, 90, 84, 243; 544/192, 201, 203

[56] References Cited

U.S. PATENT DOCUMENTS 3,700,672 10/1972 Kubuko et al. ..................... 544/203

3,979,392 9/1976 Eguchi et al. ........................ 544/203

FOREIGN PATENT DOCUMENTS 1215386 12/1970 United Kingdom ................ 544/201

Primary Examiner—Bernard Nozick
Attorney, Agent, or Firm—Sughrue, Mion, Zinn, Macpeak & Seas

[57] ABSTRACT

A method for separating liquid drops of molten urea and/or a molten mixture of urea and its thermal decomposition product from an off gas that has been freed of melamine using at least two gas-liquid separators is disclosed. The method is characterized by filling the gas-liquid separator off stream or at rest with molten urea or a molten mixture of urea and its thermal decomposition product, and at the same time, forcing the molten liquid to flow within said gas-liquid separator to remove undesired melamine iso(cyanurate) therein.

8 Claims, 1 Drawing Figure

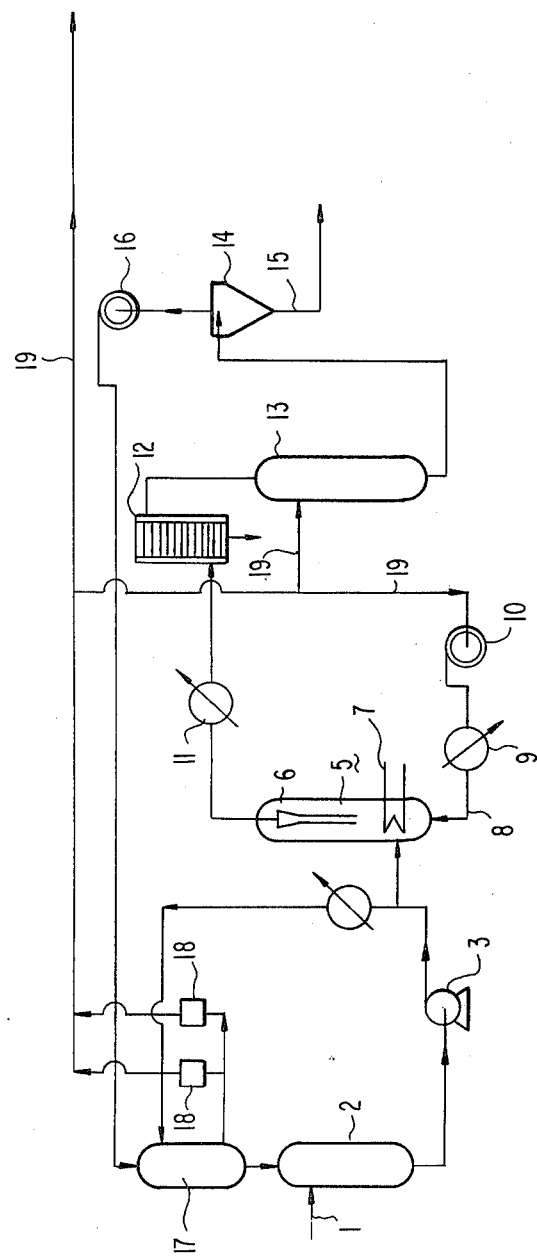

METHOD OF SEPARATING LIQUID DROPS FROM OFF GAS

FIELD OF THE INVENTION

The present invention relates to an improvement on the conventional melamine making process wherein a melamine synthesis gas produced by the thermal decomposition of urea, the thermal decomposition product of urea, or a mixture of urea and its thermal decomposition product is cooled to separate melamine by crystallization and the off gas from which melamine crystals have been separated is intimately contacted with molten urea or a mixture of urea and its thermal decomposition product to recover unreacted urea, the thermal decomposition product of urea and residual melamine by the scrubbing or washing action of the molten mass, again resulting in an off gas. The liquid drops of molten urea, the thermal decomposition product of urea, or a mixture of urea and its thermal decomposition product contained in the off gas from such recovery step are collected in a gas-liquid separator, and, before they are discharged from the separator, they are thermally decomposed into cyanuric acid or isocyanuric acid having a high melting point (the two acids being hereafter referred to as (iso)cyanuric acid), the (iso)cyanuric acid reacting with the melamine dissolved in the liquid drops of form melamine (iso)cyanurate of a high melting point that does not dissolve in the molten urea but which crystallizes, solidifies and deposits on the inner wall of the gas-liquid separator or on both the inner wall of the separator and the outer wall of a liquid drop collecting element in the separator. Therefore, the present invention specifically relates to an efficient method for removing such a melamine (iso)cyanurate salt deposit.

By the practice of the present invention, the problems with such conventional processes of melamine synthesis, such as reduced efficiency of the gas-liquid separator due to solid deposits thereon, reduced quality of the product melamine, and interrupted plant operation due to the blocking of the off gas pipe are overcome, and the plant can be run consistently over an extended period.

BACKGROUND OF THE INVENTION

Methods are known for producing melamine by the thermal decomposition of urea or its thermal decomposition product (see Japanese Patent Publications No. 4971/59, 11225/64, 1386/67, 21343/66 and 27034/69, U.S. Pat. No. 3,499,794 and *Hydrocarbon Processing*, pp. 184–186, September, 1969).

A method of separating melamine, unreacted urea and unreacted thermal decomposition product of urea from the melamine-containing synthesis gas is described in Japanese Patent Publication No. 21343/66. According to this method, the melamine synthesis gas produced by the thermal decomposition of urea or its thermal decomposition product is mixed with a cold inert gas, the mixture is cooled to a temperature at which the unreacted urea does not condense to crystallize and separate melamine. The resulting off gas substantially freed of melamine which comprises carbon dioxide, ammonia, small amounts of melamine and water vapor is intimately contacted with molten urea or a molten mixture of urea and its thermal decomposition product that is held at a temperature slightly above the melting point of urea. Unreacted urea and melamine vapor in the off gas are recovered, dissolved in or mixed with the molten mass, and part or all of the remaining off gas is recycled for use as the cold inert gas in separating melamine from the synthesis gas by crystallization.

This method permits economical recovery of the unreacted urea and melamine from the off gas and has the advantage of permitting recycle of the off gas to the mixing step after recovery of unreacted urea and melamine. However, when the off gas is recycled to the mixing step, part of the molten urea or molten mixture of urea and its thermal decomposition product accompanies the off gas in the form of liquid drops which solidify on and adhere to the inner wall of the off gas piping and the mixing vessel, and as the amount deposited increases with time, smooth operation of the system becomes impossible (see Japanese Patent Publication No. 12725/70) corresponding to British Pat. No. 1,215,836.

It is also known that if the off gas is directly recycled for mixing with the melamine synthesis gas as a cooling gas, the liquid drops of molten urea or molten mixture of urea and its thermal decomposition product in the off gas enter the melamine crystals to reduce the quality of the product melamine; see Japanese Patent Application No. (OPI) 46683/75 corresponding to U.S. Pat. No. 3,979,392 (the term "OPI" as used herein refers to a "published unexamined Japanese patent application"). It is, therefore, necessary to remove the liquid drops from the off gas before it is recycled to the mixing step.

One method which comprises using a mist separator for separating the liquid drops of molten urea or molten mixture of urea and its thermal decomposition product from the off gas is described in *Hydrocarbon Processing*, September, 1969, p. 184. Usual mist separators include ones which cause the liquid drops to settle by gravity, ones which use centrifugal force by changing the direction of the gas stream, and ones which collect the liquid drops by collision against a collecting element in the gas stream. However, when the off gas is passed through one of these mist separators, melamine (iso)cyanurate is formed as a by-product from the liquid drops of the separated molten urea or molten mixture of urea and its thermal decomposition product, and this salt adheres to the inner wall of the separator or the outer surface of the collecting element, and more salt deposits are formed with the passage of time to cause a significant reduction in gas-liquid separation efficiency. As a consequence, continuous operation of the plant over an extended period becomes difficult (see Japanese Patent Publication No. 46120/76 corresponding to U.S. Pat. No. 3,979,392.

A method has been proposed for solving these problems which comprises using two or more gas-liquid separators that collect liquid drops by centrifugal force and/or collision against a collecting element and filling them intermittently with molten urea or a molten mixture of urea and its thermal decomposition product to thereby prevent the formation of solid deposits on the inside wall of each separator or the outside surface of the collecting element (see the example of British Pat. No. 1,215,836). However, since the filling operation is not continuous it is very difficult to completely prevent buildup of the liquid drops from the off gas on the inner wall of the separator or the outer surface of the collecting element, and, as time goes by, solid deposits are formed which lower gas-liquid separation efficiency, which eventually makes continued plant operation difficult, as pointed out in Japanese Patent Application No. (OPI) 46683/75.

To overcome these difficulties, Japanese Patent Application No. (OPI) 46683/75 proposes a process wherein a gas-liquid separator that collects liquid drops by centrifugal force and/or their collision against a collecting element is used where a downwardly flowing film of molten urea or a molten mixture of urea and its thermal decomposition product is formed on the collecting surface of the separator by blowing the molten liquid onto the collecting surface or by letting it fall down along the collecting surface due to the head difference of the liquid. However, a gas-liquid separator having high separation efficiency usually has a complicated configuration and internal structure, and it is very difficult to form a uniform, consistent downwardly flowing film (laminar flow) of liquid on the surface against which the liquid drops collide.

SUMMARY OF THE INVENTION

Therefore, the primary purpose of the present invention is to provide a process wherein the melamine synthesis gas resulting from the thermal catalytic cracking of urea or its thermal decomposition product is cooled to separate melamine therefrom by crystallization and result in an off gas, the off gas from which the melamine crystals have been separated is intimately contacted with molten urea or a molten mixture of urea and its thermal decomposition product to recover unreacted urea, unreacted thermal decomposition product of urea and melamine from the off gas using the scrubbing or washing action of the molten mass, and the liquid drops of molten urea or molten mixture of urea and its thermal decomposition product are separated from the off gas in a gas-liquid separator that separates the liquid drops by gravitational settlement, centrifugal force or their collision against a collecting element.

According to the present invention, the gas-liquid separator is filled intermittently with molten urea or a molten mixture of urea and its thermal decomposition product, and, at the same time, the molten liquid is forced to flow in the separator to thereby achieve quick removal of the liquid drops or solid deposits from the inner wall of the gravitational separator or centrifugal separator which is contacted by the liquid drops or the inner wall of the collision type separator and the outer surface of the collecting element both of which are contacted by the liquid drops.

More specifically, the present invention provides a method for separating the liquid drops of molten urea and/or a molten mixture of urea and its thermal decomposition product from the off gas that has been freed of melamine using two or more gas-liquid separators, which method is characterized not only by filling the off-stream or at rest gas-liquid separator with molten urea or a molten mixture of urea and its thermal decomposition product but also by forcing the molten liquid to flow within said gas-liquid separator.

BRIEF DESCRIPTION OF THE DRAWING

FIGURE is a flow sheet of a conventional process for manufacturing melamine from urea.

DETAILED DESCRIPTION OF THE INVENTION

Separators that can be used in the practice of the present invention are those which collect liquid drops by gravitational settlement, centrifugal force or by their collision against a collecting surface. Examples include cyclone separators and baffle plate type separators. Two or more units of these separators are used in the present invention.

The molten mass with which the gas-liquid separators are filled is molten urea or a molten mixture of urea and its thermal decomposition product; the molten liquid that has been used to wash the melamine synthesis gas may also be used. If desired, the molten mass may contain a salt that reduces its melting point. Such a molten mass is supplied to two or more gas-liquid separators that are not being operated to separate the liquid drops of the molten mass from the off gas, and then discharged therefrom via an appropriate discharge valve. A molten mass is supplied to a gas-liquid separator at intervals of 2 to 6 hours, and it remains in the separator for a period of 5 to 10 minutes.

The molten mass in the separator can be agitated or caused to flow by blowing a gas therethrough, by mechanical means such as an impeller, by application of ultrasonic waves or by forced circulation with a pump. Such techniques are effective to provide maximum contact between the molten mass and the inner wall of the separator and the outer surface of the collecting element. Blowing a gas is particularly effective in removing the adhering liquid drops or solid deposits. Suitable gases include ammonia, carbon dioxide, nitrogen and mixtures thereof. A mixture of ammonia and carbon dioxide can also be used that has been separated from the off gas that has been freed of melamine by the gas-liquid separator in the melamine producing plant.

One embodiment of the process of the present invention is hereunder described by reference to the FIGURE which is a flow sheet of a conventional process for producing melamine from urea, wherein 1 is a pipe through which urea feedstock is supplied; 2 is a urea storage vessel; 3 is a pump; 4 is a pipe through which molten urea is supplied; 5 is a reactor; 6 is a cyclone separator; 7 is a heater; 8 is a carrier gas supply pipe; 9 is a gas preheater; 10 is a compressor; 11 is a gas cooler; 12 is a filter; 13 is a melamine sublimer; 14 is a melamine crystal separator; 15 is a pipe through which the product melamine is recovered; 16 is a blower; 17 is an off gas scrubber; 18 is a gas-liquid separator; and 19 is an off gas pipe.

Production of melamine is described in the prior arts described before. As one embodiment, a method for producing melamine from urea or its thermal decomposition product using the apparatus as shown in the FIGURE is described below.

Urea feedstock is supplied to the storage vessel 2 through the pipe 1. The urea is melted in the vessel 2 and part of the melt is fed to the reactor 5 by the pump 3, where it is reacted with an ammonia/carbon dioxide mixture (2:1 in volume ratio) at 350°–400° C. and 1–15 kg/cm$^2$ in a catalyst, e.g., aluminum oxide, to yield about 95% melamine.

The melamine leaves reactor 5 as a gas together with the ammonia/carbon dioxide gas, and after being cooled to about 320° C. in the gas cooler 11, is fed to the filter 12 where residual catalyst is separated from the melamine gas. The melamine gas (i.e., the synthesis gas) generally comprises ammonia, carbon dioxide, unreacted urea, melamine steam and the like, though the compositions greatly vary depending upon the thermal decomposition conditions.

The melamine gas free of residual catalyst is sent to sublimer 13 where it is cooled to about 180° to 210° C.

to crystallize the melamine. The crystalline melamine containing gas is fed to crystal separator 14 where about 99% of the melamine crystals are drawn off through the pipe 15 and packed or sent to storage.

The off gas which has been separated from the melamine crystals is sent to the scrubber 17 via blower 16 and is cooled therein to about 140° C. Unseparated solid and gaseous melamine, as well as unreacted urea, are removed from the off gas by contact with molten urea in scrubber 17. The molten urea has a temperature higher than the melting point (132° C.) of urea or higher than the azeotropic point of the thermal decomposition product comprising urea and the biuret, and at the temperature of which the flowability of the molten urea is maintained and the thermal decomposition does not proceed rapidly. The resulting off gas which is substantially ammonia and carbon dioxide is passed through gas-liquid separator 18 for separating any liquid drops in the gas, and part of it is recycled via pipe 19 to reactor 5 and the balance forwarded to sublimer 13. The gas-liquid separator (mist separator) which can be used in the present invention is described, for example, in Perry, *Chemical Engineers Handbook*, the paragraph of "Phase Separation", 3rd Edition.

In the practice of the present invention, two or more (generally 2-8, preferably 4-6) gas-liquid separators 18 are used, and, to remove the liquid drops or their solidified product from the inner wall of the separator, the inner wall of the separator which is off-stream or the outer surface of the collecting element therein is wetted with molten urea or a molten mixture of urea and its thermal decomposition product, and, at the same time, the molten mass is agitated or caused to flow by any of the methods described above. According to the process of the present invention, reduction in the efficiency of gas-liquid separation and reduction in the quality of the product melamine due to the solid deposits on the inner wall of the gas-liquid separator and the outer surface of the collecting element therein, as well as interrupted operation due to the blocking of the off gas piping system, are avoided, and consistent plant operation is assured for an extended period of time.

The present invention is now described in greater detail by reference to the following examples to which the invention is by no means limited.

EXAMPLES 1a and 1b

A melamine synthesis gas (320° C.) supplied from reactor 5 at a rate of 40 kg/hr was mixed with off gas (138° C.) that was made up of 50 vol% ammonia and 50 vol% carbon dioxide which was recycled via pipe 19 from contact with the molten urea. The resulting gas mixture was cooled to 210° C., whereby melamine was crystallized in the gaseous phase and the melamine crystals were separated from the off gas in crystal separator 14 and recovered via pipe 15. The melamine-free off gas was fed to scrubber 17 (gas-liquid laminate flow contact type) where it was intimately contacted with a molten mixture (135° C.) of urea (77 wt%), biuret (20 wt%) and cyanuric acid (3 wt%), and was cooled to 138° C. The unreacted urea and melamine in the off gas were caught by the molten mixture. The off gas as contacted by the molten mass contained 5 to 20 $g/m^3$ of liquid drops. To remove these liquid drops, the off gas was passed through 4 units (18, 18, . . . ) of zig-zag baffle plate type impingement mist separators (Example 1a) or cyclone mist separators (Example 1b) each capable of collecting liquid drops by their own inertial force, the centrifugal force due to a change in the direction of the gas stream and by their collision against a collecting element in the separator. Every two hours the off-stream separator, i.e., the one that was not operating, was filled with a molten mixture of urea and its thermal decomposition product for 10 minutes, while, at the same time, ammonia gas whose pressure was 4 $kg/cm^2$ was bubbled into the molten mixture from below the separator 18 at a rate of 0.1 kg/hr to force the molten mixture to turbulently flow within the separator. The 4 units of separator were thus treated in turns, and the number of days which the melamine producing plant was continuously operated until the gas-liquid separation efficiency of any separator (18) decreased to 80% its initial value was checked. The results are shown in Table 1.

EXAMPLES 2a and 2b

Examples 1a and 1b were repeated except that the gas blown into the separator was a mixture of ammonia and carbon dioxide (2:1 by volume ratio) rather than ammonia gas. The results of checking gas-liquid separation efficiency are also shown in Table 1.

EXAMPLES 3a and 3b

Examples 1a and 1b were repeated except that the gas blown into the separator was carbon dioxide rather than ammonia. The results of checking gas-liquid separation efficiency are shown in Table 1.

EXAMPLE 4a

Example 1a was repeated except that the molten mixture of urea and its thermal decomposition product was not only bubbled with ammonia but also agitated with a turbine impeller at the bottom of the separator. The results of checking gas-liquid separation efficiency are shown in Table 1.

COMPARATIVE EXAMPLES 1a and 1b

Examples 1a and 1b were repeated except that the separators were not filled with the molten mixture of urea and its thermal decomposition product nor were they bubbled with ammonia gas. The results of checking gas-liquid separation efficiency are shown in Table 1.

COMPARATIVE EXAMPLES 2a and 2b

Examples 1a and 1b were repeated except that the separator at rest was filled with the molten mixture of urea and its thermal decomposition product but was not bubbled with ammonia gas. The results of checking gas-liquid separation efficiency are shown in Table 1.

EXAMPLE 5a

Example 4a was repeated except that the molten mixture was agitated with a turbine impeller but was not bubbled with ammonia gas. The results of gas-liquid separation efficiency are shown in Table 1.

The data in Table 1 demonstrate that by agitating the molten mixture within the separator or forcing it to flow, the gas-liquid separation efficiency of the separators can be maintained at a high level for a prolonged period of time.

TABLE 1

|  | Mist Separator* | | What Was Done to the Mist Separator* | | | Mist** |
|---|---|---|---|---|---|---|
|  | Baffle Plate Type Impingement Separator | Cyclone Separator | Filled with Molten Liquid | Molten Liquid Bubbled with Gas | Molten Liquid Agitated with Turbine Impeller | Separation Efficiency (days) |
| Example 1a | o |  |  | $NH_3$ |  | 150 |
| Example 1b |  | o | o | " |  | 150 |
| Example 2a | o |  | o | $NH_3 + CO_2$ |  | 130 |
| Example 2b |  | o | o | " |  | 130 |
| Example 3a | o |  | o | $CO_2$ |  | 100 |
| Example 3b |  | o | o | " |  | 100 |
| Example 4a | o |  | o | $NH_3$ | o | 150 |
| Example 5a | o |  | o |  | o | 100 |
| Comparative Example 1a | o |  | o |  |  | 15 |
| Comparative Example 1b |  | o |  |  |  | 20 |
| Comparative Example 2a | o |  | o |  |  | 25 |
| Comparative Example 2b |  | o | o |  |  | 30 |

**The number of days before the mist separation efficiency decreased to 80%.

While the invention has been described in detail and with reference to specific embodiments thereof, it will be apparent to one skilled in the art that various changes and modifications can be made therein without departing from the spirit and scope thereof.

What is claimed is:

1. A method for separating liquid drops of molten urea, the thermal decomposition product of urea or a mixture of molten urea and its thermal decomposition product from a melamine synthesis off gas using at least two gas-liquid separators by alternately passing off gas to a separator to separate liquid drops of urea or the thermal decomposition product of urea or a mixture of urea and its decomposition product wherein each of said separators has a collecting element, a means for ingress and egress for said molten urea, said thermal decomposition product, or said mixture, and said off gas, wherein at least one gas-liquid separator is on-stream, and at least one gas-liquid separator is off-stream where the off gas has been freed of melamine, which comprises supplying the off-stream gas-liquid separator with molten urea or a molten mixture of urea and its thermal decomposition product, hereinafter collectively referred to as molten mass, and allowing said molten mass to remain in the separator and at the same time providing a turbulent means for said molten mass to flow within said off-stream gas-liquid separator and then discharging said molten mass from said separator thereby removing said liquid drops from said separator by said drops having been contacted by said molten mass.

2. A method according to claim 1, wherein the molten liquid is forced to flow by agitating it with an impeller.

3. A method according to claim 1, wherein the gas-liquid separator is of the type which uses gravitational force to separate the liquid drops of a molten mass from a gas stream by settlement of said drops.

4. A method according to claim 1, wherein the gas-liquid separator is of the type which uses the centrifugal force caused by changing the direction of a gas stream.

5. A method according to claim 1, wherein the gas-liquid separator is of the type which collects the liquid drops by their collision against a collecting element in a gas stream.

6. A method according to claim 1, wherein the molten liquid is forced to flow by blowing a gas thereinto.

7. A method according to claim 6, wherein said gas is ammonia, carbon dioxide or a mixture thereof.

8. In a method for separating unreacted urea from an off gas resulting from the separation of melamine by crystallization from a member selected from the group consisting of a melamine synthesis gas containing unreacted urea, the thermal decomposition product of urea, and a mixture of the melamine synthesis gas and the thermal decomposition product of urea, wherein said off gas is contacted with molten urea or a molten mixture of urea and its thermal decomposition product, hereinafter collectively referred to as molten mass, to recover unreacted urea, the improvement which comprises:

(a) using two or more gas-liquid separators alternately, wherein each of said separators has a collecting element, a means for ingress and egress for said molten urea, said thermal decomposition product, said mixture, said molten mass, and said off gas;

(b) at least one of said gas-liquid separators being on-stream wherein said off-gas is contacted with said molten urea said thermal decomposition product, or said mixture of molten urea and its thermal decomposition product resulting in the formation of solid drops of melamine (iso)cyanurate salt on the wall of said on-stream gas-liquid separator;

(c) at least one of said gas-liquid separators being off-stream after having previously been on stream and having accumulated deposits of the melamine (iso)cyanurate salt on its wall wherein said molten mass is introduced filling the off-stream separator and at the same time turbulently caused to flow in the separator whereby said solid deposits of the melamine (iso)cyanurate salt are dissolved; and (d) said molten mass is discharged from the separator and thereafter said off-stream separator is put back on-stream and the on-stream generator upon a predetermined accumulation of said solid drops of melamine (iso)cyanurate salt deposit on the wall is switched off-stream to remove said solid drops per step (c).

* * * * *